United States Patent [19]
Chesterfield et al.

[11] Patent Number: 5,403,331
[45] Date of Patent: Apr. 4, 1995

[54] LOOPED SUTURE LIGATING DEVICE CONTAINING A HEAT-SHRINKABLE ELEMENT

[75] Inventors: Michael P. Chesterfield, Norwalk; Thomas D. Guy, Fairfield; Mark S. Roy, Enfield, all of Conn.

[73] Assignee: United States Surgical Corporation, Norwalk, Conn.

[21] Appl. No.: 30,746

[22] Filed: Mar. 12, 1993

[51] Int. Cl.⁶ .............................................. A61B 17/00
[52] U.S. Cl. ...................... 606/148; 606/139; 606/151; 606/158
[58] Field of Search ............................ 606/110–113, 606/103, 139, 144, 148, 151, 157, 158, 232

[56] References Cited
U.S. PATENT DOCUMENTS

| | | | |
|---|---|---|---|
| 3,476,114 | 11/1969 | Shannon et al. | |
| 3,476,115 | 11/1969 | Graeff et al. | |
| 3,665,926 | 5/1972 | Flores | 606/139 |
| 4,016,881 | 4/1977 | Rioux et al. | 606/51 |
| 4,018,229 | 4/1977 | Komiya | 606/139 |
| 4,313,245 | 2/1982 | Yamaguchi | 24/205.16 R |
| 5,053,041 | 10/1991 | Ansari et al. | 606/148 |
| 5,129,912 | 7/1992 | Noda | |
| 5,133,738 | 7/1992 | Korthoff et al. | |
| 5,144,961 | 9/1992 | Chen et al. | |
| 5,171,251 | 12/1992 | Bregen et al. | 606/151 |
| 5,236,434 | 8/1993 | Callicrate | 606/139 |

FOREIGN PATENT DOCUMENTS

| | | | |
|---|---|---|---|
| 477020 | 3/1992 | European Pat. Off. | |
| 0975006 | 11/1982 | U.S.S.R. | 606/139 |
| 1393408 | 5/1988 | U.S.S.R. | 606/148 |

*Primary Examiner*—Stephen C. Pellegrino
*Assistant Examiner*—Jeffrey A. Schmidt

[57] ABSTRACT

A surgical device for use in a ligating procedure in which a looped suture is slidably secured by a securement member. In a preferred embodiment a loop is formed in a suture and the end of the suture is slidably secured relative to the suture body portion by a shrinkable tubing. One or more slip knots are contemplated within or adjacent the shrinkable tubing. The second suture end may be secured to a shaft member in a traditional manner.

21 Claims, 3 Drawing Sheets

LOOPED SUTURE LIGATING DEVICE CONTAINING A HEAT-SHRINKABLE ELEMENT

FIELD OF THE INVENTION

The present invention relates to surgical ligating devices, and more particularly to ligatures for use in endoscopic or laparoscopic procedures.

BACKGROUND OF THE INVENTION

Ligating devices have been successfully used in surgical procedures for many years. One such device has a looped suture disposed at the end of a tubular shaft and means for drawing the suture loop to a tightly closed position at a desired location in the surgical site. See, for example, U.S. Pat. Nos. 3,476,114 and 3,476,115. A typical problem with the manufacture and operation of such ligature devices is that the suture loop must be secured by a one-way knot. That is, the loop must be free to contract but, at the same time, resist any subsequent enlargement. Such one-way knots can require complex manipulation of the suture portion to form the knot, making the manufacture of such ligatures to be a complicated and costly process.

Therefore, it would be desirable to provide a ligating device which either requires no knot or a simple knot which is easier and less costly to manufacture than presently available devices.

SUMMARY OF THE INVENTION

By way of satisfying the foregoing object as well as other objects of the invention, there is provided in accordance with this invention a ligating device which comprises:

a) a suture having two end portions and a body portion disposed therebetween;

b) a substantially cylindrical shaft member having a proximal end, a distal end, a longitudinal passage therethrough and at least a portion of the suture disposed therein;

c) a loop in the suture disposed distally of the distal end of the shaft member, the loop at least partially formed by doubling-back one of the suture end portions; and d) a securement member disposed distally of the distal end of the shaft member and proximally of the suture loop, the securement member surrounding a portion of the suture body portion and a portion of the doubled-back suture end portion to at least partially slidably secure the end portion relative to the suture body portion.

In a preferred embodiment, the present invention includes a ligating device as previously described wherein the securement member is a heat shrinkable tubular member and a relatively uncomplicated slip knot is disposed within the shrinkable tube. During operation, a surgeon can use the device of the present invention in the same manner as with other known ligature devices. However, under the present invention, the method of manufacturing the device is much simplified due to the use of the securement member in enhancing the securement of the suture loop, and elimination of any need for a complex one-way slip knot.

BRIEF DESCRIPTION OF DRAWINGS

The present invention will become more apparent from the following detailed description taken in conjunction with the accompanying drawings.

DETAILED DESCRIPTION OF THE PREFERRED EMBODIMENTS

Figure 1A:
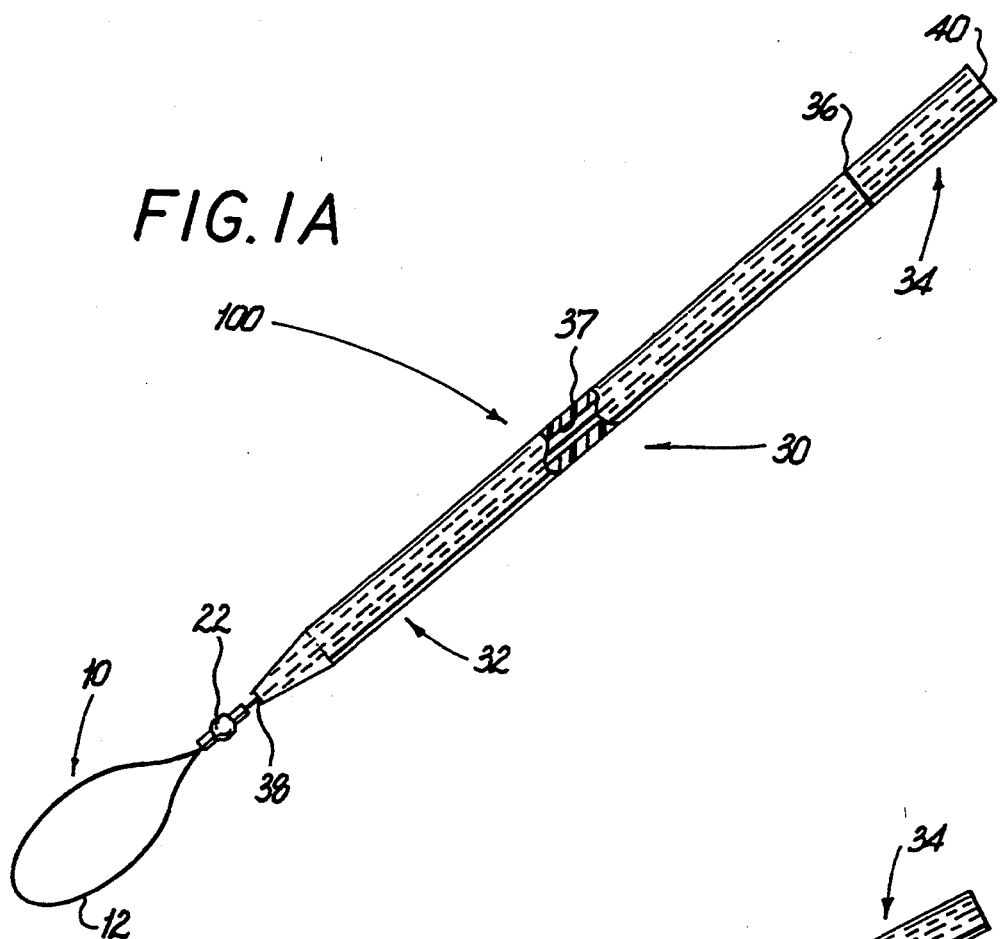
FIG. 1A illustrates an embodiment of the looped suture ligating device of the present invention wherein a looped suture portion is disposed at the end of a substantially cylindrical, tubular shaft.

Referring now in specific detail to the drawings, in which like reference numerals identify similar or identical elements, the looped suture ligating device of the present invention is shown in FIG. 1A, indicated generally by 100. The device includes suture portion 10 and substantially cylindrical, tubular shaft 30. Shaft 30 comprises a distal shaft portion 32 and a proximal shaft portion 34 connected at a weakened section 36. Generally cylindrical channel 37 (in phantom) defines a longitudinal, generally central passage in shaft 30. Shaft 30 can be of any suitable material, preferably plastic and most preferably nylon.

The suture portion of device 100, generally denoted by 10, includes suture 12 and tubular member 22 as a securement member. Suture 12 has a suture body portion 14 and suture end portions 16 and 18 (see FIGS. 2 and 3A). Loop portion 20 is formed by doubling-back suture end portion 18, adjacent body portion 14, and then by securing suture end portion 18 adjacent suture body portion 14 by a tubular securement member 22. Tubular securement member 22, with suture end portion 18 disposed therein, is slidable with respect to suture body portion 14. In FIG. 1A, suture body portion 14 enters shaft 30 at aperture 38, passes through central channel 37 of shaft 30 and suture end portion 16 is secured to proximal shaft portion 34 at 40.

Figure 1B:
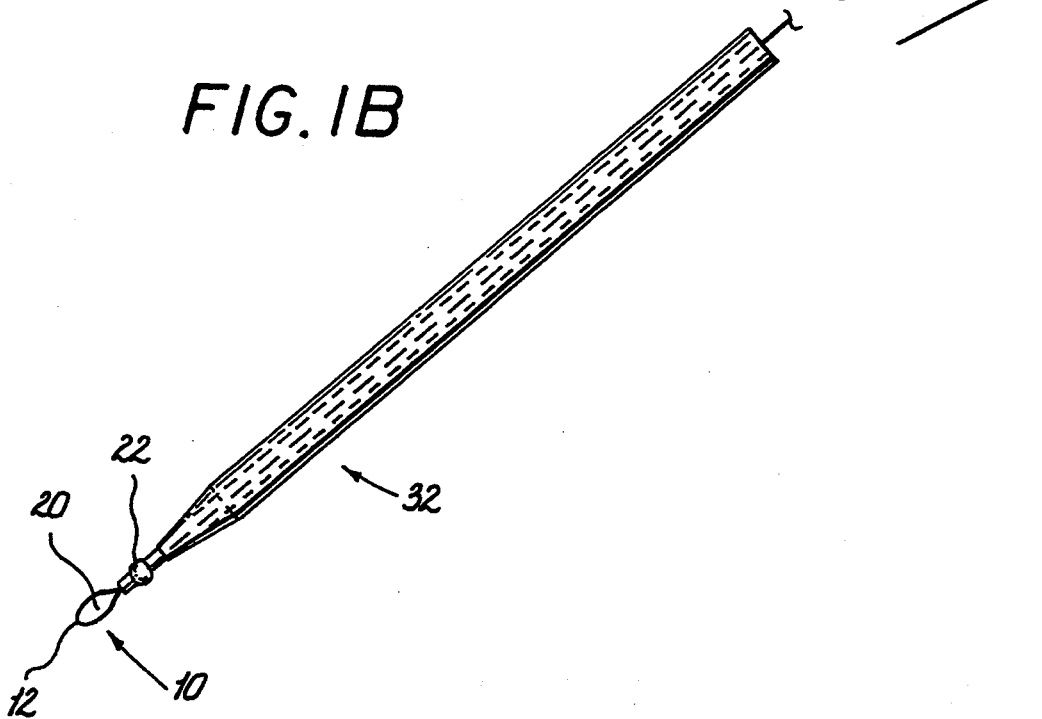
FIG. 1B illustrates the device of FIG. 1A after partial contraction of the suture loop.

Referring to FIG. 1B, during use a surgeon will insert ligating device 100 into a body cavity and cause loop 20 to become positioned about an anatomical structure or organ to be ligated or constricted. The body cavity can be accessed by means of conventional/open surgery or by endoscopic means, such as through a cannula assembly. (See, for example, U.S. Pat. Nos. 4,902,280 and 5,116,353.) With the anatomical structure surrounded by loop 20, the surgeon will break tubular shaft 30 at weakened section 36, thereby separating distal shaft portion 32 from proximal shaft portion 34. By drawing shaft portion 34 and attached suture end portion 16 away from the proximal end of shaft portion 32, the surgeon will cause suture body portion 14 to slide through the center of shaft portion 32 such that tubular securement member 22 abuts the distal end of shaft portion 32. On further pulling of the suture, suture body portion 14 slides through tubular securement member 22, causing loop portion 20 to contract about the anatomical structure. When loop portion 20 is contracted to a desired size and tension tubular securement member 22 prevents subsequent enlargement of the loop portion, thereby effecting secure ligation of the anatomical structure. Finally, a cutting device will be used to sever the suture adjacent to tubular securement member 22.

Suture 12 can be fabricated of either bioabsorbable materials, such as gut material or synthetic polymeric resins, or of non-bioabsorbable biocompatible materials. Suitable bioabsorable polymeric resins include, for example, homopolymers and copolymers derived from members of the group consisting of polyglycolic acid, glycolide, lactic acid, lactide, dioxanone, caprolactone, trimethylene carbonate and mixtures thereof. Polymers and copolymers of the foregoing kind and absorbable surgical devices made therefrom are well known. See, e.g., U.S. Pat. Nos. 3,297,033; 3,636,956; 3,736,646; 3,839,297; 4,052,988; and 5,019,093. Examples of suitable non-bioabsorbable biocompatible materials include homopolymers and copolymers of polypropylenes, silks, polyamides, polyesters, polyvinyl chlorides, and polysulfones. Materials of the foregoing kind are well known. See, e.g., U.S. Pat. Nos. 3,630,205; 4,911,165; and 5,102,419. Suture 12 may include suitable dyes, coatings, plasticizers, fillings, etc. as desired or appropriate to improve the visibility and/or handling characteristics of the suture.

Figure 2:
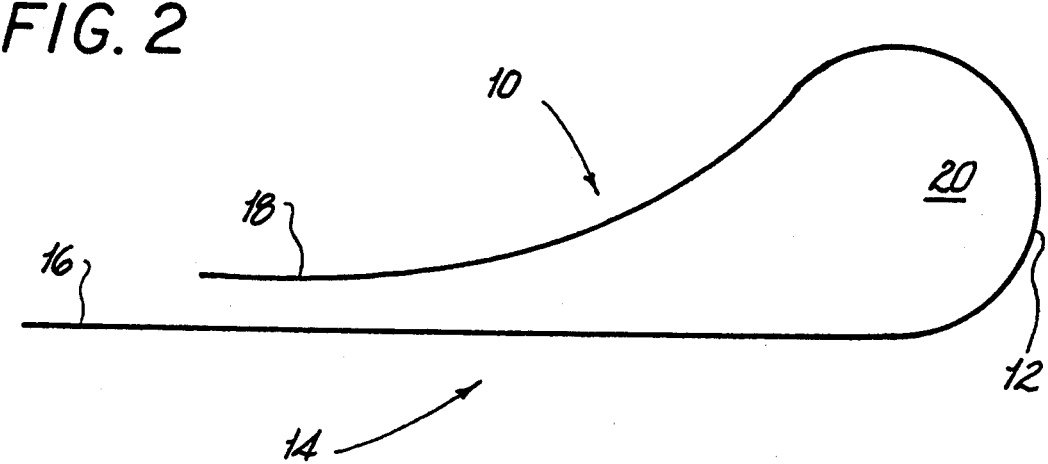
FIG. 2 illustrates a suture with one end portion doubled-back to form a loop.

Turning more specifically to the looped suture portion of the present invention, with reference to FIG. 2, looped suture 10 includes suture 12, suture body portion 14 and suture end portions 16 and 18. End portion 18 is doubled-back adjacent to a portion of the suture body portion 14 so as to form loop 20 in suture 12.

Figure 3A:
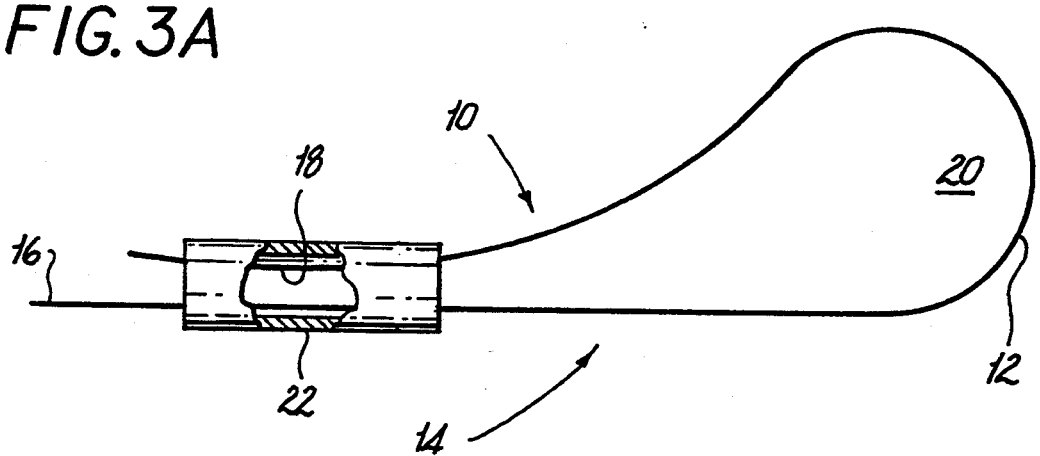
FIG. 3A illustrates the suture of FIG. 2 wherein a securement member is disposed around portions of both the suture body portion and the doubled-back end portion.

FIG. 3A illustrates the looped suture of FIG. 2 wherein tubular securement member 22 of sufficient inner diameter has been slid onto and surrounds suture body portion 14 and suture end portion 18 to define loop 20. Suture body portion 14 is slidable relative to suture end portion 18 and securement member 22. Of course, the tubular securement member could also be placed around suture body portion 14 before suture end portion 18 is doubled-back, with suture end portion 18 thereafter doubled-back and inserted into the securement member.

Securement member 22 can be fabricated from any material suitable for securing the suture in a one-way, slidable loop formation. Such materials should be suitable for in vivo implantation, which include, for example, stainless steel, titanium and absorbable and non-absorbable polymers or combinations thereof. Securement member 22 is preferably colored to facilitate visualization during surgical procedures. If the securement member is made of metal, it can be compressed or crimped around the suture body and end portion so as to hold the suture end portion and yet permit sliding of the suture body relative to the securement member.

In a preferred embodiment, securement member 22 is tubular and made of heat shrinkable material so that it can be shrunken by heat subsequent to being positioned on suture 12 to slidably secure suture end portion 18 relative to suture body portion 14. Suitable materials which shrink, i.e., reduce in diameter in response to the application of energy, include biocompatible "memory metals," e.g., nickel-titanium mixtures, nickel-iron-titanium mixtures, or copper based materials, as are well known in the art (see e.g., U.S. Pat. Nos. 3,757,552; 3,801,95; 4,198,081 and 4,773,680), and shrinkable plastic materials, such as polyvinylidene fluoride, available from Raychem Corporation, Menlo Park, Calif., under the trade name "KYNAR". In the case of shrinkable plastic materials, the tubing is typically extruded such that the inner diameter is less than the final desired inner diameter, i.e., the inner diameter of the tubing after energy application in the attachment method of the present invention. Thereafter, extruded tubing is expanded radially outward through radial expansion means to provide a tubing of expanded inner diameter as shown, for example, by tubing 22 in FIG. 3A. Such plastic tubing is thus adapted to shrink or "recover" to its original extruded inner diameter in response to the application of a predetermined amount of energy.

The amount of energy applied to the tubing to affect the desired attachment, i.e., diameter reduction, depends upon the chemical characteristics of the tubing material, the relative dimensions of the tubing, the type of suture material used, the type or alternative knots used in conjunction with the tubing, and the desired pull force necessary to tighten the suture loop of the ligating device. For example, one polyvinylidene fluoride material available from Raychem Corporation (RT-850) shrinks at temperatures greater than 175° C., and is adapted to recover to about 50% of its radially expanded inner diameter. In such a case, tubular securement member 22, after being slid onto suture body portion 14 and suture end portion 18, may be tightened by heating securement member 22 to a temperature of 175° C. Heat may be applied by means of contact with a hot gas stream or with heated dyes, or by other heating means. This engagement of the securement member and the suture portions provides the novel suture loop securement means of the present invention.

Figure 3B:
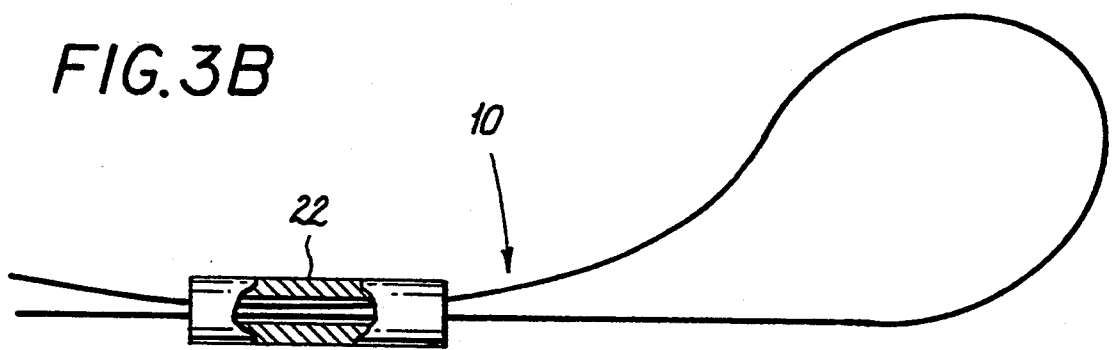
FIG. 3B illustrates the looped suture of FIG. 3A wherein the securement member is shrunken to grasp portions of both the suture body portion and doubled-back end portion.

FIG. 3B shows tubular securement member 22 shrunken around the doubled-back suture end portion, thereby slidably securing the end portion relative to the suture body portion.

Figure 4:
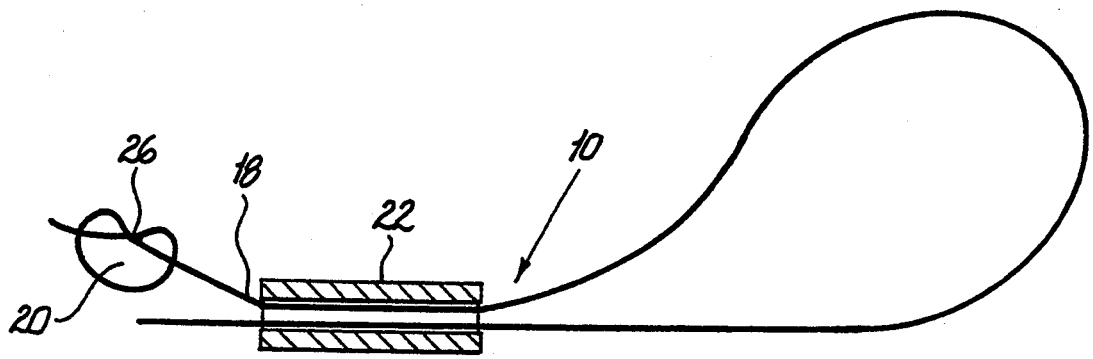
FIG. 4 illustrates a first alternative embodiment of the looped suture of FIG. 3B with a knot tied in the end of the doubled-back end portion.

In a first alternative embodiment, shown in FIG. 4, doubled-back end portion 18 has knot 26 tied in the end portion on the side of tubular securement member 22 opposite that of loop 20. The purpose of this knot is to provide added securement of doubled-back end portion 18 to further prevent the end portion from pulling back through securement member 22 during surgical ligation procedures.

Figure 5A:
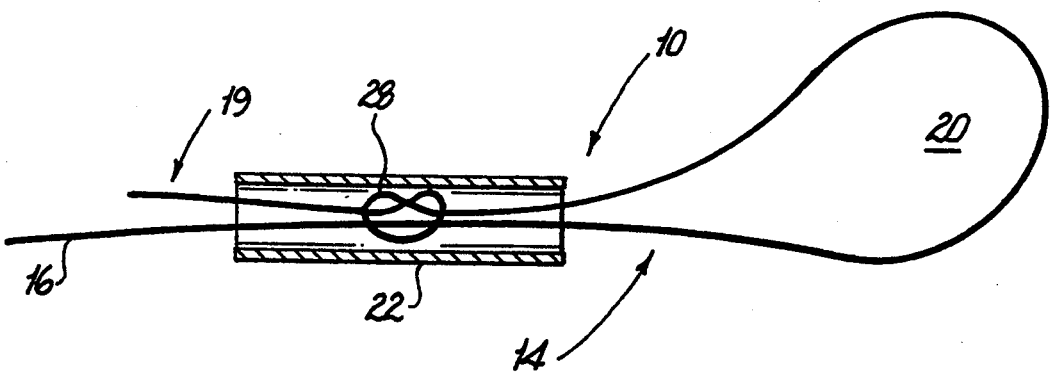
FIG. 5A illustrates a second alternative embodiment of the looped suture of FIG. 3A wherein the end portion has a slip knot tied around the body portion of the suture and the knot is disposed within the securement member.
Figure 5B:
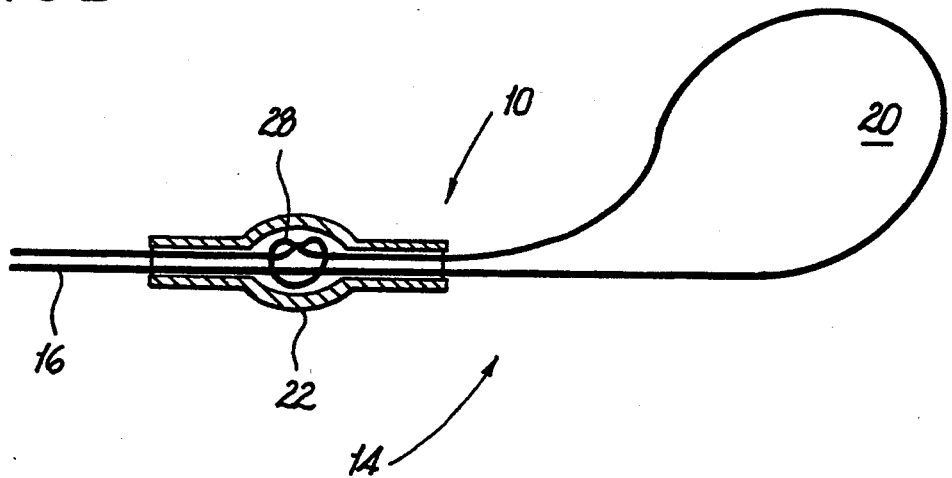
FIG. 5B illustrates the looped suture of FIG. 5A wherein the securement member is shrunken around the slip knot.

In a most preferred embodiment shown in FIGS. 5A–5B, doubled-back end portion 18 forms slip knot 28 tied about suture body portion 14. Slip knot 28 in this embodiment is a simple overhand knot tied in end portion 18 through which suture body portion 14 passes. Tubular securement member 22 is then slipped over knot 28 (FIG. 5A) and may then be shrunken by heat (FIG. 5B) as previously discussed. Either before or after securement member 22 is shrunken by heat, the non-functional piece of doubled-back end portion 18 which hangs out of securement member 22, depicted as 19, may be trimmed. Various other slip knots can also be used and are considered to be within the scope of the present invention. For example, an alternative slip knot is a common two half hitch knot. In contrast with slip knots approaching the complexity of knots presently used to form looped ligating devices, the securement member of the present invention advantageously permits a simple slip knot, which is more efficient to form during manufacture, to be used.

While the invention has been particularly shown and described with reference to the preferred embodiments, it will be understood by those skilled in the art that various modifications in form and detail may be made therein without departing from the scope and spirit of the invention. Accordingly, such modifications are to be considered within the scope of the invention as defined by the claims.

What is claimed is:

1. A method of making a looped suture ligating device which comprises:
   a) providing a suture having two end portions and a body portion disposed therebetween;
   b) doubling-back one of said end portions to form a loop in said suture body portion;
   c) positioning a securement member fabricated from a heat shrinkable material around a portion of said suture body portion and said doubled-back end portion such that said doubled-back end portion is disposed adjacent to and in contacting relationship with said suture body portion within said securement member, thereby at least partially securing said doubled-back end portion relative to said body portion; and
   d) heating said securement member to slidably secure said doubled-back end portion relative to said suture body portion.

2. A method of making a looped suture ligating device which comprises:
   a) providing a suture having two end portions and a body portion disposed therebetween;
   b) doubling-back one of said end portions to form a loop in said suture body portion;
   c) positioning a securement member around a portion of said suture body portion and said doubled-back end portion such that said doubled-back end portion is disposed adjacent to and in contacting relationship with said suture body portion within said securement member, thereby at least partially securing said doubled-back end portion relative to said body portion; and
   d) tying a knot in said double-backed end portion such that said suture body portion is slidable through said knot.

3. The method of claim 2 wherein said knot is disposed within said securement member.

4. The method of claim 2 wherein said knot is disposed adjacent to said securement member.

5. The method of claim 1 further comprising securing said second suture end portion to a shaft member.

6. A looped suture ligating device which comprises:
   a) a suture having two end portions and a body portion disposed therebetween;
   b) a substantially cylindrical shaft member having a proximal end, a distal end, a longitudinal passage therethrough and at least a portion of said suture disposed therein;
   c) a loop in said suture disposed distally of said distal end of said shaft member, said loop at least partially formed by doubling-back one of said suture end portions; and
   d) a substantially tubular securement member disposed distally of said distal end of said shaft member and proximally of said suture loop, said securement member surrounding a portion of said suture body portion and a portion of said doubled-back suture end portion to at least partially slidably secure said end portion relative to said suture body portion, said securement member being made from a heat shrinkable material.

7. The device of claim 6 wherein said shrinkable material comprises polyvinylidene fluoride.

8. The device of claim 6 wherein said securement member is made of a biocompatible metal.

9. The device of claim 6 further comprising preventing means for preventing said doubled-back suture end portion from passing through said securement member.

10. The device of claim 9 wherein said preventing means comprises a knot in said doubled-back suture end portion.

11. The device of claim 6 further comprising a knot in said doubled-back end portion wherein said suture body portion is slidable within said slip knot.

12. The device of claim 11 wherein said slip knot is disposed within said securement member.

13. The device of claim 11 wherein said knot is disposed adjacent to said securement member.

14. The device of claim 11 wherein said doubled-back suture end portion is sufficiently constricted by said shrunken securement member so as not to pull through said securement member during ligation procedures.

15. The device of claim 6 wherein said shaft member comprises a first shaft portion and a second shaft portion, said shaft portions connected at a weakened section, and one of said suture end portions is secured to one of said shaft portions.

16. A looped suture ligature comprising:
   a) a suture having a body portion and at least one end portion;
   b) a substantially tubular member surrounding a portion of said suture body portion and said end portion to define a loop and to slidably secure said suture body portion relative to said suture end portion, said tubular member comprising a heat shrinkable material and a single aperture passing therethrough, each said suture portions passing through said single aperture.

17. The ligature of claim 16 wherein said shrinkable material comprises polyvinylidene fluoride.

18. The ligature of claim 16 further comprising a knot in said end portion formed about said suture body portion.

19. The ligature of claim 18 wherein said knot is disposed within said tubular member.

20. The ligature of claim 18 wherein said knot is disposed adjacent to said tubular member.

21. The ligature of claim 16 wherein said suture body portion is slidable within said tubular member so as to permit a decrease in the size of said loop portion.

* * * * *